(12) United States Patent
Su et al.

(10) Patent No.: US 9,651,434 B2
(45) Date of Patent: May 16, 2017

(54) PRESSURE ARRAY SENSOR MODULE AND MANUFACTURING METHOD THEREOF AND MONITORING SYSTEM AND MONITORING METHOD USING THE SAME

(71) Applicant: Industrial Technology Research Institute, Chutung, Hsinchu (TW)

(72) Inventors: Jui-Yiao Su, New Taipei (TW); Yan-Chen Liu, Taipei (TW); Chang-Yi Chen, Hsinchu (TW); Ching-Shun Chen, Changhua County (TW); Wen-Ching Ko, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/873,949

(22) Filed: Oct. 2, 2015

(65) Prior Publication Data

US 2016/0097689 A1    Apr. 7, 2016

(30) Foreign Application Priority Data

Oct. 3, 2014 (TW) .............................. 103134541 A
Jul. 14, 2015 (TW) .............................. 104122718 A (51) Int. Cl.
*G01D 7/00* (2006.01)
*G01L 1/20* (2006.01)
(Continued)

(52) U.S. Cl.
CPC ............ *G01L 1/205* (2013.01); *A61B 5/1036* (2013.01); *A61B 5/6807* (2013.01); *A61B 5/6892* (2013.01);
(Continued)

(58) Field of Classification Search
CPC ..... G01L 1/205; A61B 5/1036; A61B 5/6807; A61B 5/6892; A61B 2562/0247; A61B 2562/046; A61G 2203/34
(Continued)

(56) References Cited

U.S. PATENT DOCUMENTS 4,444,998 A     4/1984  House
4,640,137 A *   2/1987  Trull ...................... G01L 5/228
                                                      338/114
(Continued)

FOREIGN PATENT DOCUMENTS

CN      101263373 A    9/2008
CN      102371586 A    3/2012
(Continued)

OTHER PUBLICATIONS

K. Kim et al., "Polymer-based flexible tactile sensor up to 32×32 arrays integrated with interconnection terminals," Sensors and Actuators A, 156, (2009), pp. 284-291.
(Continued)

*Primary Examiner* — Max Noori
(74) *Attorney, Agent, or Firm* — Muncy, Geissler, Olds & Lowe, P.C.

(57) ABSTRACT

A pressure array sensor module including an array electrode board, a plurality of pressure sensing elements, at least one first conductive structure and at least one second conductive structure is provided. The array electrode board includes a substrate and an array electrode. The array electrode, disposed on the substrate, has a first electrode pattern and a second electrode pattern. Each pressure sensing element, disposed on a sensing position of the array electrode board, includes a top electrode layer, a bottom electrode layer and at least one pressure sensing layer disposed between the top and bottom electrode layers. The top electrode layer has a
(Continued)

first lead. The bottom electrode layer has a second lead. The first conductive structure is electrically connected between each first lead and a corresponding first electrode pattern. The second conductive structure is electrically connected between each second lead and a corresponding second electrode pattern.

26 Claims, 9 Drawing Sheets

(51) Int. Cl.
*A61B 5/103* (2006.01)
*A61B 5/00* (2006.01)
(52) U.S. Cl.
CPC . *A61B 2562/0247* (2013.01); *A61B 2562/046* (2013.01)
(58) Field of Classification Search
USPC .................................. 73/862.041–862.046
See application file for complete search history.

(56) References Cited

U.S. PATENT DOCUMENTS

| | | | | |
|---|---|---|---|---|
| 5,010,774 | A * | 4/1991 | Kikuo | B25J 13/084 338/114 |
| 5,237,879 | A | 8/1993 | Speeter | |
| 5,373,747 | A | 12/1994 | Ogawa et al. | |
| 5,736,656 | A | 4/1998 | Fullen et al. | |
| 5,799,533 | A | 9/1998 | Seki et al. | |
| 6,964,205 | B2 | 11/2005 | Papakostas et al. | |
| 7,258,026 | B2 | 8/2007 | Papakostas et al. | |
| 7,926,364 | B2 | 4/2011 | Joung | |
| 7,926,366 | B2 | 4/2011 | Yang et al. | |
| 7,973,274 | B2 | 7/2011 | Kuniyoshi et al. | |
| 8,653,837 | B2 | 2/2014 | Frangen | |
| 8,788,093 | B2 | 7/2014 | Sakakibara et al. | |
| 2001/0047246 | A1 * | 11/2001 | Fullen | A43D 1/025 702/33 |
| 2010/0050784 | A1 * | 3/2010 | Joung | G01L 5/228 73/862.046 |
| 2014/0088764 | A1 | 3/2014 | Naidu et al. | |
| 2014/0130593 | A1 * | 5/2014 | Ciou | A61B 5/1038 73/172 |
| 2016/0097688 | A1 * | 4/2016 | Chen | G01L 1/005 73/774 |

FOREIGN PATENT DOCUMENTS

| | | |
|---|---|---|
| CN | 103528604 A | 1/2014 |
| EP | 1947436 A1 | 7/2008 |
| JP | 57-198839 A | 12/1982 |
| JP | 58-79126 A | 5/1983 |
| JP | 64-61626 A | 3/1989 |
| JP | 2569433 B1 | 1/1997 |
| JP | 2001-343296 A | 12/2001 |
| JP | 3286852 B2 | 3/2002 |
| JP | 2003-344185 A | 12/2003 |
| JP | 2005-27983 | 2/2005 |
| JP | 2005-77228 A | 3/2005 |
| JP | 2011-53115 | 3/2011 |
| JP | 4868347 B2 | 2/2012 |
| JP | 2013178241 A | 9/2013 |
| JP | 5765901 B2 | 6/2015 |
| JP | 2016-75657 A | 5/2016 |
| TW | I237801 | 8/2005 |
| TW | I-200742139 | 11/2007 |
| TW | I306051 | 2/2009 |
| TW | I306054 | 2/2009 |
| TW | 200921074 A | 5/2009 |
| TW | I309195 | 5/2009 |
| TW | 201015055 A | 4/2010 |
| TW | 201116366 A | 5/2011 |
| TW | 201216302 A | 4/2012 |
| TW | I385366 | 2/2013 |
| TW | 201310011 | 3/2013 |
| TW | I476633 | 3/2015 |
| TW | M-516781 U | 2/2016 |

OTHER PUBLICATIONS

CMA Ashruf, "Thin flexible pressure sensors," Sensor Review, vol. 22, Issue 4, (2002), pp. 322-327.
Papakostas, T.V., et al., "5.3: A Large Area Force Sensor for Smart Skin Applications," Proc 1st IEEE Sensors Conf, 2002, pp. 1620-1624.
M. Shimojo et al., "A Tactile Sensor Sheet Using Pressure Conductive Rubber With Electrical-Wires Stitched Method," IEEE Sensors Journal, vol. 4, No. 5, Oct. 2004, pp. 589-596.
ES Hwang et al., "A Polymer-Based Flexible Tactile Sensor, For Normal And Shear Load Detection," MEMS 2006, Istanbul, Turkey, Jan. 22-26, 2006, pp. 714-717.
T. Mukai et al., "Development of the Tactile Sensor System of a Human-Interactive Robot 'RI-MAN'", IEEE Transactions on Robotics, vol. 24, No. 2, Apr. 2008, pp. 505-512.
HK Lee et al., "A Flexible Polymer Tactile Sensor: Fabrication and Modular Expandability for Large Area Deployment," Journal of Microelectromechanical Systems, vol. 15, No. 6, Dec. 2006, pp. 1681-1686.
TM Anandan, "Safety and control in collaborative robotics," http://controleng.com/single-article/safety-and-control-in-collaborative-robotics/6fec60e21f303fa660c81bb2584236f8.html, Aug. 6, 2013, 7 pp.
M. Vasic et al., "Safety Issues in Human-Robot Interactions," 2013 IEEE International Conference on Robotics and Automation (ICRA), May 6-10, 2013, pp. 197-204.
D. Stengel et al., "An Approach for Safe and Efficient Human-Robot Collaboration," SIAS 2010, Jun. 14, 2010, 6 pp.
P.A. Lasota et al., Toward Safe Close-Proximity Human-Robot Interaction with Standard Industrial Robots, IEEE CASE 2014, Aug. 18, 2014, 6 pp.
S. Haddadin et al., Requirements for Safe Robots: Measurements, Analysis and New Insights, The Internatinal Hournal of Robotics Research OnlineFirst, Aug. 20, 2009, pp. 1-21.
K. Eder et al., Towards the Safety of Human-in-the-Loop Robotics: Challenges and Opportunities for Safety Assurance of Robotic Co-Workers, The $23^{rd}$ IEEE International Symposium on Robot and Human Interactive Communication, Aug. 25, 2014, 7 pp.

* cited by examiner

PRESSURE ARRAY SENSOR MODULE AND MANUFACTURING METHOD THEREOF AND MONITORING SYSTEM AND MONITORING METHOD USING THE SAME

This application claims the benefits of Taiwan application Serial No. 103134541, filed Oct. 3, 2014, and Taiwan application Serial No. 104122718, filed Jul. 14, 2015, the disclosures of which are incorporated by reference herein in its entirety.

TECHNICAL FIELD

The disclosure relates in general to a sensor module and system, and more particularly to a pressure array sensor module and a manufacturing method thereof and a monitoring system and a monitoring method using the same.

BACKGROUND

Pressure sensor is mainly used to detect a pressure which generates a stress on an element. The pressure array sensing technology can be used to detect the change in the distribution and geometric gradient of pressure when an element receives a pressure. For example, the pressure array sensing technology can be used in a shoe pad for detecting the pressure distribution of the foot or can used in a mattress for detecting the pressure distribution and gravity trace of the one sleeping on the mattress.

The screen printing process most commonly used in the thin-type pressure array sensor module has three processes. Firstly, an array electrode pattern is designed in advance according to the needs of application, and the screens required in the processes for manufacturing an electrode layer, a pressure sensing layer and an adhesive layer are manufactured. Then, the electrode layer, the pressure sensing layer and adhesive layer are printed on a substrate by repeating the screen printing process for three times. Then, the elements are aligned and assembled to manufacture a pressure array sensor module. However, when the density of the sensing elements needs to be customized or adjusted, all screens need to be re-designed and the screen printing process need to be repeated for three times again. Since each design change involves a considerable amount of time and cost, it is difficult to reduce manufacturing time and cost.

SUMMARY

The disclosure is directed to a pressure array sensor module and a manufacturing method thereof for resolving the problems encountered in the prior art.

The disclosure is directed to a monitoring system using a pressure array sensor module and a monitoring method thereof, such as a monitoring system and a monitoring method used for analyzing the collision or contact on a surface of an object.

According to one embodiment, a pressure array sensor module is provided. The pressure array sensor module includes an array electrode board, a plurality of pressure sensing elements, at least one first conductive structure and at least one second conductive structure. The array electrode board includes a substrate and an array electrode. The array electrode is disposed on the substrate, and has a first electrode pattern and a second electrode pattern. Each pressure sensing element is disposed on a sensing position of the array electrode board, and includes a top electrode layer, a bottom electrode layer and at least one pressure sensing layer. The top electrode layer has a first lead, and the bottom electrode layer has a second lead. The pressure sensing layer is disposed between the top electrode layer and the bottom electrode layer. The first conductive structure is electrically connected between each first lead and a corresponding first electrode pattern. The second conductive structure is electrically connected between each second lead and a corresponding second electrode pattern.

According to one embodiment, a manufacturing method for a pressure array sensor module is provided. The manufacturing method includes following steps. An array electrode having a first electrode pattern and a second electrode pattern is formed on a substrate. A plurality of pressure sensing elements are disposed on the substrate, wherein each pressure sensing element has a top electrode layer, a bottom electrode layer and at least one pressure sensing layer disposed between the top electrode and the bottom electrode. Each lead of the top electrode layer and a corresponding first electrode pattern are electrically connected by at least one first conductive structure. Each lead of the bottom electrode layer and a corresponding second electrode pattern are electrically connected by at least one second conductive structure.

According to one embodiment, a monitoring system is provided. The monitoring system includes the said pressure array sensor module, a control module and a voltage detecting unit. The control module includes a first switch circuit, a second switch circuit and a voltage detecting unit. The first switch circuit includes a first parallel switch capable of electrically connecting several first signal circuits extended to the first switch circuit from the array electrode at the same time, such that the first signal circuits are mutually connected in parallel. The second switch circuit includes a second parallel switch capable of electrically connecting several second signal circuits extended to the second switch circuit from the array electrode at the same time, such that the second signal circuits are mutually connected in parallel. The voltage detecting unit has an input end and an output end. The input end electrically connects the first signal circuits through the first switch circuit. The output end electrically connects the second signal circuits through the second switch circuit. The input end has an input voltage. The output end has an output voltage. The voltage detecting unit detects an equivalent resistance of the pressure sensing elements connected in parallel between the first signal circuits and the second signal circuits according to the input voltage and the output voltage.

According to one embodiment, a monitoring method is provided. The monitoring method includes following steps. A control module and a pressure array sensor module are provided, wherein the pressure array sensor module is disposed on a surface of an object. Whether to perform a collision detection loop or a self-detection loop on the pressure array sensor module by the control module is determined. When the control module selects to perform the collision detection loop by using the said monitoring system, the collision detection loop detects a variation in an equivalent resistance of the pressure sensing elements with respect to an initial equivalent resistance. When the control module selects to perform the self-detection loop by using the said monitoring system, the self-detection loop detects a variation in each resistance of the scanned pressure sensing elements with respect to a reference resistance. The first parallel switch of the collision detection loop and the first scan switch of the self-detection loop share but do not use the first signal circuits at the same time. The second parallel switch of the collision detection loop and the second scan switch of the self-detection loop share but do not use the second signal circuits at the same time.

The above and other aspects of the invention will become better understood with regard to the following detailed description of the preferred but non-limiting embodiment(s). The following description is made with reference to the accompanying drawings.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

A number of embodiments are disclosed below for elaborating the disclosure. However, the embodiments are for exemplary and explanatory purpose only, not for limiting the scope of protection of the invention.

First Embodiment

Figure 1A:
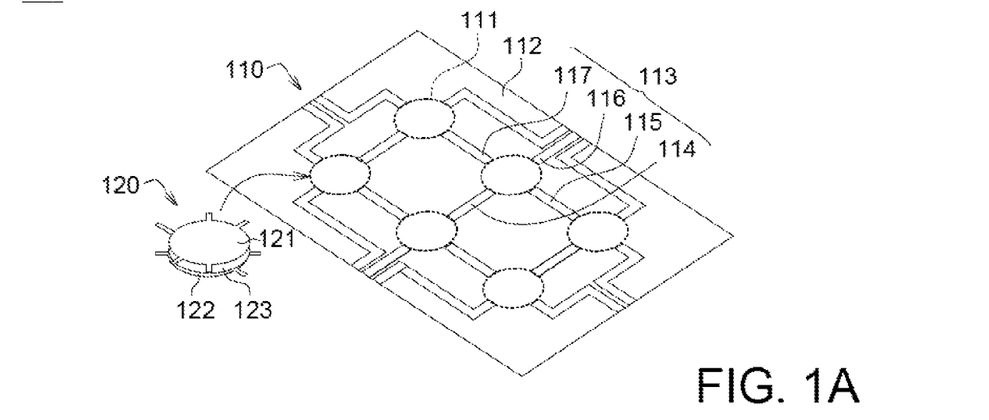
FIG. 1A is a schematic diagram of a pressure array sensor module according to an embodiment.
Figure 1B:
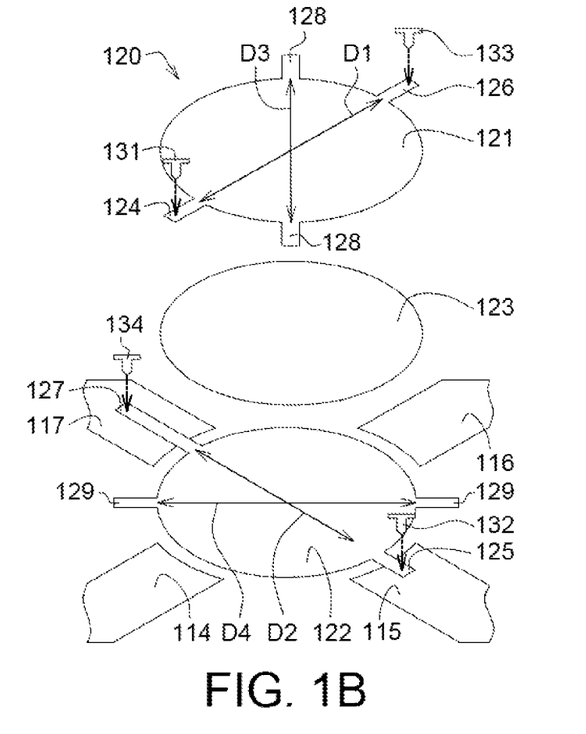
FIG. 1B is a structural decomposition diagram of a pressure sensing element.

Refer to FIGS. 1A and 1B. FIG. 1A is a schematic diagram of a pressure array sensor module 100 according to an embodiment. FIG. 1B is a structural decomposition diagram of a pressure sensing element 120.

In an embodiment, the pressure array sensor module 100 includes an array electrode board 110, a plurality of pressure sensing elements 120 (only one pressure sensing element is illustrated), a first conductive structure 131 and a second conductive structure 132. Each pressure sensing element 120 can be electrically connected to the array electrode board 110 through the first conductive structure 131 and the second conductive structure 132.

As indicated in FIG. 1A, the array electrode board 110 includes a substrate 112 and an array electrode 113. The array electrode 113 is disposed on one side or two opposite sides of the substrate 112, and the patterns of the array electrode are printed on the substrate 112 by using a screen printing process. The array electrode 113 has several electrode patterns 114~117 whose circuit layout is based on customer-specific requirements. The substrate 112 can be a flexible insulating film or a printed circuit board, and the array electrode 113 is disposed around each sensing position 111.

In an embodiment, when the array electrode 113 is disposed on two opposite sides of the substrate 112, a sensing position 111 on each side can be adjusted according to the change in the position of the array electrode 113, such that the sensing positions 111 on two opposite sides can be staggered. Thus, more pressure sensing elements 120 can be disposed on the array electrode board 110 to increase the sensing density (that is, the quantity of elements per unit area is increased).

In FIG. 1A, the pressure sensing elements 120 are disposed on the sensing positions 111 (6 sensing positions 111 are exemplified) of the array electrode board 110, that is, in the blank positions defined by electrode patterns. The pressure sensing elements 120 are independent elements. Even when the design of electrode patterns is adjusted according to customer-specific requirements, the pressure sensing elements 120, having been manufactured independently, can be disposed on the sensing positions 111 defined by the electrode patterns. Thus, the position or density distribution of each pressure sensing element 120 can be easily changed according to customer-specific requirements without having to manufacture the screens again or perform the screen printing process on the sensing elements.

In FIG. 1A, the array electrode 113 includes a first electrode pattern 114, a second electrode pattern 115, a third electrode pattern 116 and a fourth electrode pattern 117. The first electrode pattern 114 is extended between two sensing positions 111 as a wire conducting two pressure sensing elements 120 on corresponding positions. Similarly, the second electrode pattern 115 is extended between two sensing positions 111 as a wire conducting two pressure sensing elements 120 on corresponding positions. The extending directions of the first electrode pattern 114 and the second electrode pattern 115 can be orthogonal, non-orthogonal or parallel to each other. FIG. 1A only illustrates the arrangement in which the extending directions of the first electrode pattern 114 and the second electrode pattern 115 are orthogonal to each other, but the disclosure does not have specific restrictions.

In FIG. 1A, the extending directions of the first electrode pattern 114 and the third electrode pattern 116 are parallel to each other, and so are the extending directions of the second electrode pattern 115 and the fourth electrode pattern 117 parallel to each other. In another embodiment, the extending directions of the first electrode pattern 114 and the third electrode pattern 116 are not parallel to each other. As indicated in FIG. 1B, the extending direction of the first electrode pattern 114 is parallel to the first direction D1. When the extending direction of the third electrode pattern 116, which was originally parallel to the first direction D1, changes to be parallel to the third direction D3, the extending directions of the first electrode pattern 114 and the third electrode pattern 116 are not the same. As indicated in FIG. 1B, the extending direction of the second electrode pattern 115 is parallel to the second direction D2. When the extending direction of the fourth electrode pattern 117, which was originally parallel to the second direction D2, changes to be parallel to the fourth direction D4, the extending directions of the second electrode pattern 115 and the fourth electrode pattern 117 are not the same. Therefore, the directions of the said electrode patterns 114~117 are adjustable.

Refer to FIG. 1B. The pressure sensing elements 120 includes a top electrode layer 121, a bottom electrode layer 122 and at least one pressure sensing layer 123. The top electrode layer 121 has a first lead 124 corresponding to the first electrode pattern 114, such that the first lead 124 and the first electrode pattern 114 overlap in a vertical direction (the normal direction of the substrate 112). Similarly, the bottom electrode layer 122 has a second lead 125 corresponding to the second electrode pattern 115, such that the second lead 125 and the second electrode pattern 115 overlap in a vertical direction (the normal direction of the substrate 112). The pressure sensing layer 123 is disposed between the top electrode layer 121 and the bottom electrode layer 122, such that the top electrode layer 121, the pressure sensing layer 123 and the bottom electrode layer 122 overlap in a vertical direction (the normal direction of the substrate 112).

In FIG. 1B, the first lead 124 of each pressure sensing element 120 and the first electrode pattern 114 are electrically connected through the first conductive structure 131, and the second lead 125 and the second electrode pattern 115 are electrically connected through the second conductive structure 132. Therefore, the two adjacent pressure sensing elements 120 can be electrically connected in series through the first electrode pattern 114 and two first conductive structures 131 disposed at two ends of the first electrode pattern 114, such that the modularization requirements can be satisfied. Furthermore, the two adjacent pressure sensing elements 120 can be electrically connected in series through the second electrode pattern 115 and two second conductive structures 132 disposed at two ends of the second electrode pattern 115.

In FIG. 1B, the top electrode layer 121 may further have a third lead 126 corresponding to the third electrode pattern 116, such that the third lead 126 and the third electrode pattern 116 overlap in a vertical direction (the normal direction of the substrate 112). Similarly, the bottom electrode layer 122 may further have a fourth lead 127 corresponding to the fourth electrode pattern 117, such that the fourth lead 127 and the fourth electrode pattern 117 overlap in a vertical direction (the normal direction of the substrate 112).

In FIG. 1B, the third lead 126 of each pressure sensing element 120 and the third electrode pattern 116 are electrically connected through the third conductive structure 133, and the fourth lead 127 and the fourth electrode pattern 117 are electrically connected through the fourth conductive structure 134. Therefore, the top electrode layer 121 of each pressure sensing element 120 is connected in series between the first electrode pattern 114 and the third electrode pattern 116 through the first conductive structure 131 and the third conductive structure 133 respectively, such that the modularization requirements can be satisfied. Similarly, the bottom electrode layer 122 of each pressure sensing element 120 is connected in series between the second electrode pattern 115 and the fourth electrode pattern 117 through the second conductive structure 132 and the fourth conductive structure 134 respectively, such that the modularization requirements can be satisfied.

In FIG. 1B, the top electrode layer 121 can electrically connect the first electrode pattern 114 and/or the third electrode pattern 116 at different directions by using the leads 128 instead of the first lead 124 and/or the third lead 126 disclosed above. That is, when the first electrode pattern 114 and/or the third electrode pattern 116 change directions, the first electrode pattern 114 and the third electrode pattern 116 can be connected through corresponding leads 128 (one or a pair). Thus, there is no need to manufacture new pressure sensing elements 120, hence reducing the manufacturing cost. In another embodiment, the first lead 124 and the third lead 126 can be used with another two leads 128 at the same time or alternately, or with one, two, or three of the above four leads, and the present disclosure does not have specific restrictions.

Similarly, in FIG. 1B, the bottom electrode layer 122 can electrically connect the second electrode pattern 115 and/or the fourth electrode pattern 117 at different directions by using the leads 129 instead of the second lead 125 and/or the fourth lead 127 disclosed above. That is, when the directions of the second electrode pattern 115 and/or the fourth electrode pattern 117 are changed, the second electrode pattern 115 and the fourth electrode pattern 117 can be connected through corresponding leads 129 (one or a pair). Thus, there is no need to manufacture new pressure sensing elements 120, hence reducing the manufacturing cost. In another embodiment, the second lead 125 and the fourth lead 127 can be used with another two leads 129 at the same time or alternately, or with one, two, or three of the above four leads, and the present disclosure does not have specific restrictions.

Second Embodiment

Figure 2A:
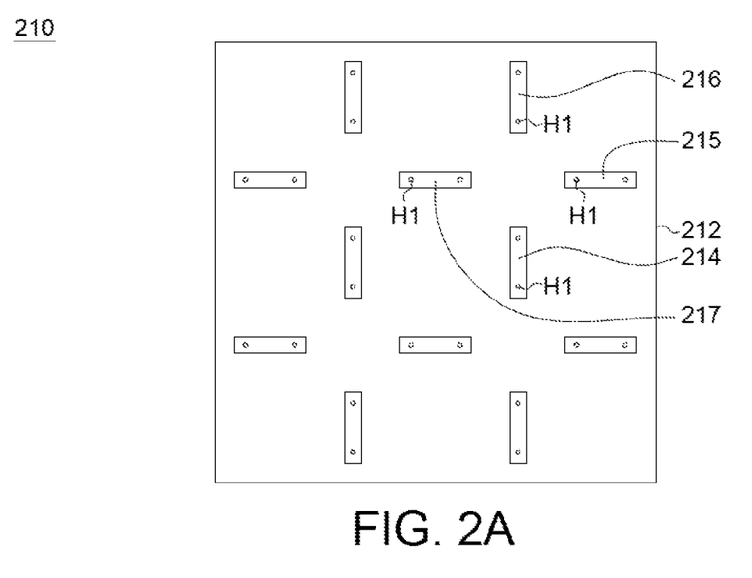
FIG. 2A is a schematic diagram of an array electrode board according to an embodiment.
Figure 2B:
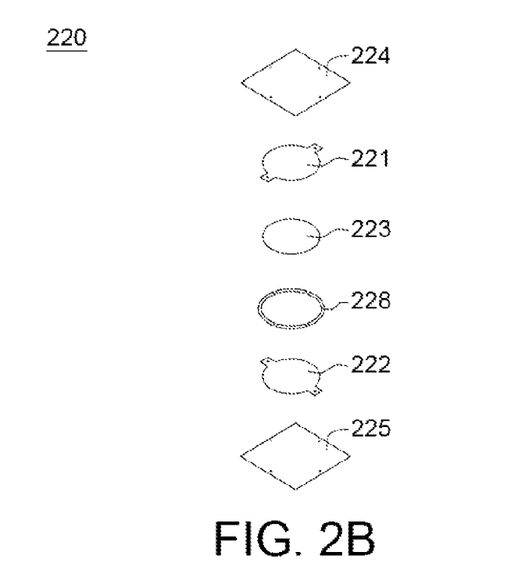
FIG. 2B is a structural decomposition diagram of a pressure sensing element.
Figure 2C:
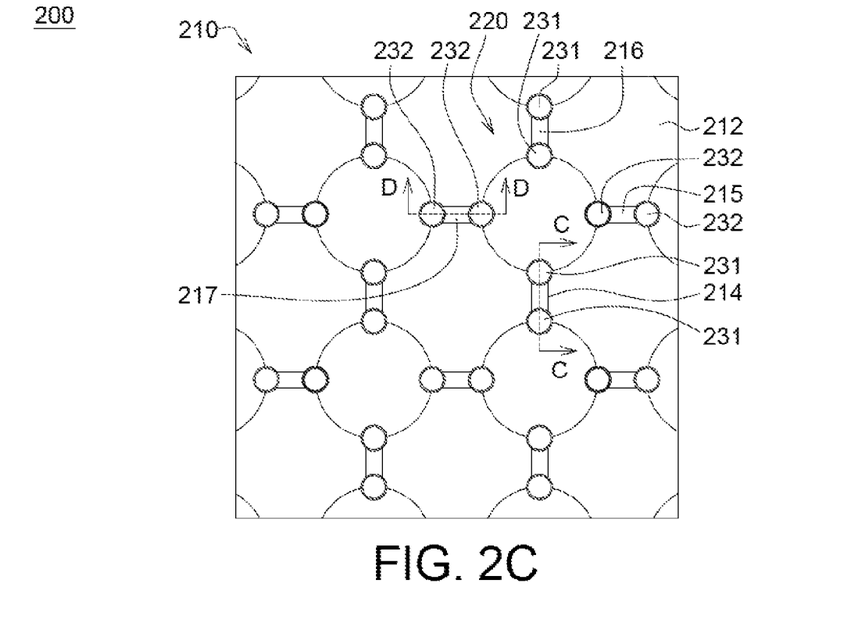
FIG. 2C is a schematic diagram of a plurality of pressure sensing elements disposed on the array electrode board.

Refer to FIGS. 2A-2C. FIG. 2A is a schematic diagram of an array electrode board 210 according to an embodiment. FIG. 2B is a structural decomposition diagram of a pressure sensing element 220. FIG. 2C is a schematic diagram of a plurality of pressure sensing elements 220 disposed on the array electrode board 210. In FIG. 2B, the pressure sensing elements 220 includes a top substrate 224, a top electrode layer 221, at least one pressure sensing layer 223, a bottom electrode layer 222, a bottom substrate 225 and a plurality of engaging portions 228. The engaging portions 228 are separated from each other and form an arc which engages the top substrate 224 and the bottom substrate 225, such that the top electrode layer 221, the pressure sensing layer 223 and the bottom electrode layer 222 are stacked between the top substrate 224 and the bottom substrate 225. Besides, the leads 226 and 227 of the top electrode layer 221 and the bottom electrode layer 222 can pass through the gap between two adjacent engaging portions 228 as indicated in FIG. 3.

Figure 3:
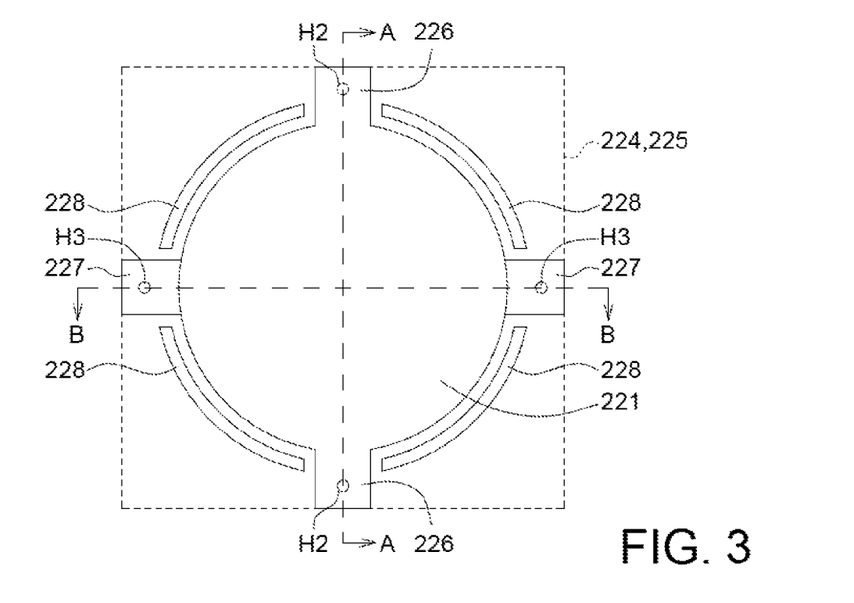
FIG. 3 is a top view of an assembled pressure the sensing element of FIG. 2B.
Figure 4A:
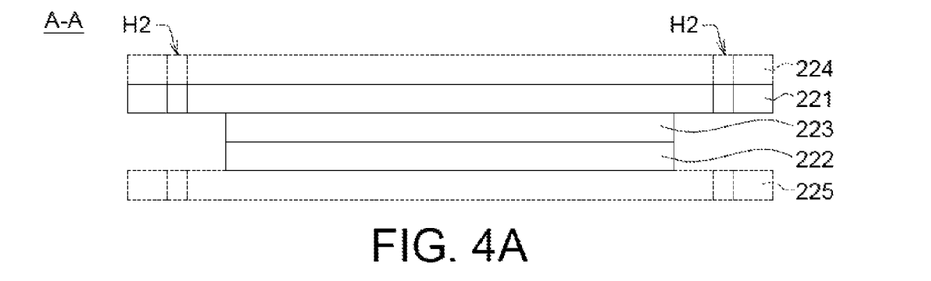
FIG. 4A is a cross-sectional view along a cross-sectional line A-A of FIG. 3.
Figure 4B:
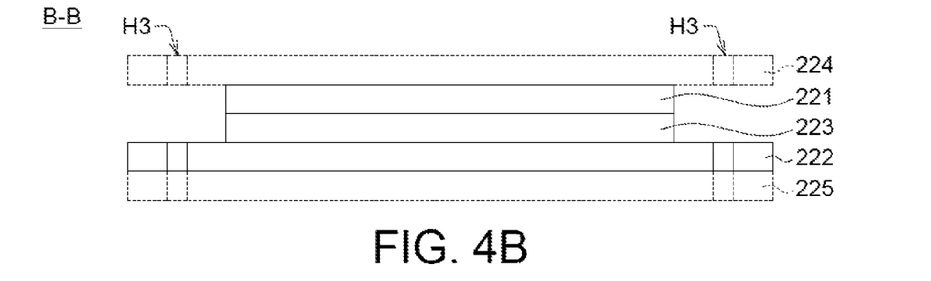
FIG. 4B is a cross-sectional view along a cross-sectional line B-B of FIG. 3.

Refer to FIG. 3 and FIGS. 4A and 4B. FIG. 3 is a top view of an assembled pressure sensing element 220 of FIG. 2B. FIG. 4A is a cross-sectional view along a cross-sectional line A-A of FIG. 3. FIG. 4B is a cross-sectional view along a cross-sectional line B-B of FIG. 3. To more clearly illustrate the structural relationship between elements, the top substrate 224 and the bottom substrate 225 are denoted by dotted lines.

As indicated in FIG. 2A, several first through holes H1 are formed on the array electrode board 210 and pass through the electrode patterns 214~217 and the substrate 212 at the same time. Moreover, as indicated in FIGS. 2B, 3 and 4A-4B, several second through holes H2 and third through holes H3 are formed on the pressure sensing elements 220. The second through holes H2 pass through the top substrate 224, the top electrode layer 221 and the bottom substrate 225 at the same time. The third through holes H3 pass through the top substrate 224, the bottom electrode layer 222 and the bottom substrate 225 at the same time. The second through holes H2 and the third through holes H3 correspond to the first through holes H1 of the array electrode board 210.

As indicated in FIG. 3, the second through holes H2 correspond to the leads 226 passing through the top electrode layer 221, and the third through holes H3 correspond to the leads 227 passing through the bottom electrode layer 222. The leads 226 of the top electrode layer 221 can be the first lead 124 and the third lead 126 disclosed above or another two leads 128, and the leads 227 of the bottom electrode layer 222 can be the second lead 125 and the fourth lead 127 disclosed above or another two leads 129.

Figure 5A:
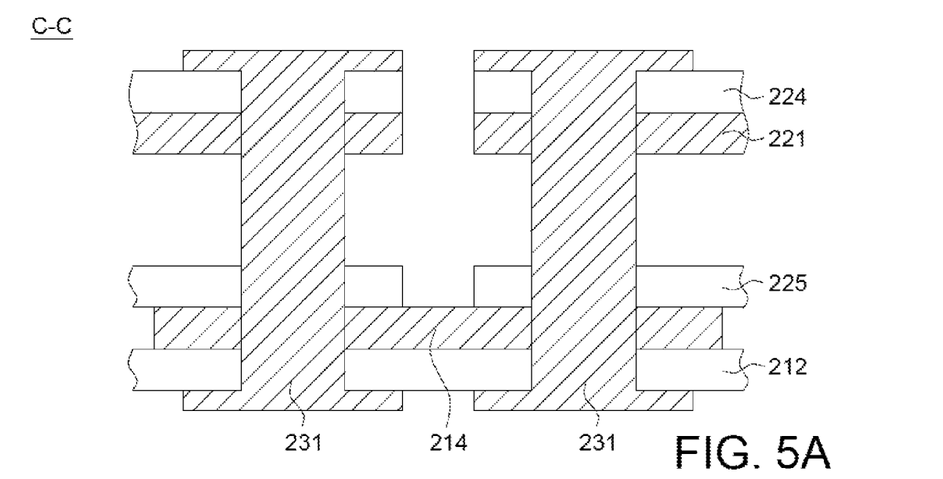
FIG. 5A is a cross-sectional view along a cross-sectional line C-C of FIG. 3.

Referring to FIG. 5A, a cross-sectional view along a cross-sectional line C-C of FIG. 2C is shown. In FIG. 2C, several vertical conductive elements 231 pass through the second through holes H2 of the pressure sensing elements 220 (referring to FIG. 4A) and the first through holes H1 of a corresponding array electrode board 210 (referring to FIG. 2A) to form a pressure array sensor module 200. As indicated in FIG. 5A, each vertical conductive element 231 sequentially passes through the top substrate 224, the top electrode layer 221, the bottom substrate 225, the electrode pattern 214 and the substrate 212 in a top down manner, and makes the top electrode layer 221 and the electrode pattern 214 vertically conducted. Therefore, adjacent two of the pressure sensing elements 220 can be electrically connected in series through an electrode pattern 214 and two vertical conductive elements 231 disposed at two ends of the electrode pattern 214, such that the modularization requirements can be satisfied. The same arrangement can be applied on the electrode pattern 216 and is not repeated here.

The electrode pattern 214 can be the first electrode pattern 114 or the third electrode pattern 116 disclosed above, and the vertical conductive elements 231 can be the first conductive structure 131 or the third conductive structure 133 disclosed above.

Figure 5B:
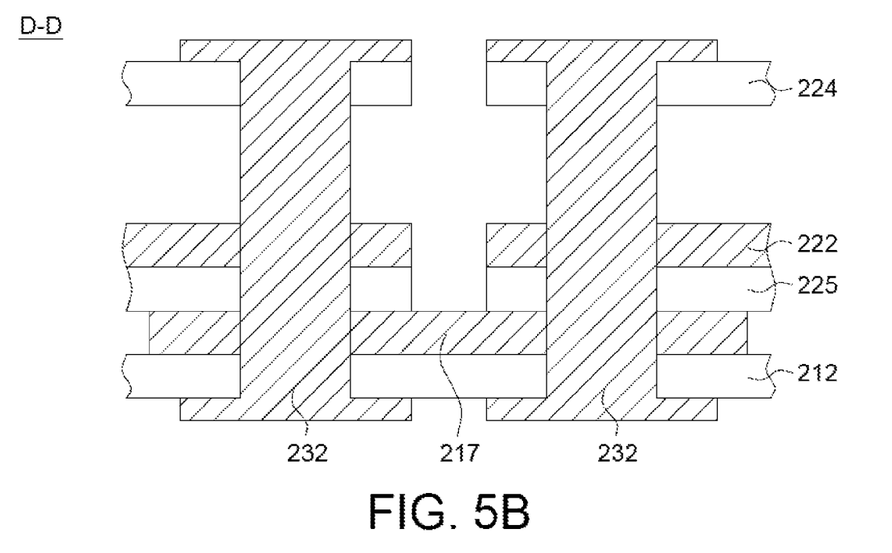
FIG. 5B is a cross-sectional view along a cross-sectional line D-D of FIG. 2C.

Referring to FIG. 5B, a cross-sectional view along cross-sectional line D-D of FIG. 2C is shown. In FIG. 2C, several vertical conductive elements 232 pass through the third through holes H3 of the pressure sensing elements 220 (referring to FIG. 4B) and the first through holes H1 of a corresponding array electrode board 210 (referring to FIG. 2A) to form a pressure array sensor module 200. In FIG. 5B, each vertical conductive element 232 sequentially passes through the top substrate 224, the bottom electrode layer 222, the bottom substrate 225, the electrode pattern 217 and the substrate 212 in a top down manner, such that the bottom electrode layer 222 and the electrode pattern 217 are vertically conducted. Therefore, adjacent two of the pressure sensing elements 220 can be electrically connected in series through an electrode pattern 217 and two vertical conductive elements 232 disposed at two ends of the electrode pattern 217. The same arrangement can be applied on the electrode pattern 215 and is not repeated here.

The electrode pattern 217 can be used as the second electrode pattern 115 or the fourth electrode pattern 117 disclosed above, and the vertical conductive elements 232 can be used as the second conductive structure 132 or the fourth conductive structure 134 disclosed above. The vertical conductive elements 231 and 232 can be formed of a metal, an alloy, a tin paste or an anisotropic conductive material. If the vertical conductive elements 231 and 232 are formed of a conductive adhesive or a tin paste, the conductive adhesive or the tin paste passes through the holes and solidifies into columns, such that the pressure sensing elements 220 and the array electrode board 210 are tightly engaged as one piece.

Figure 5C:
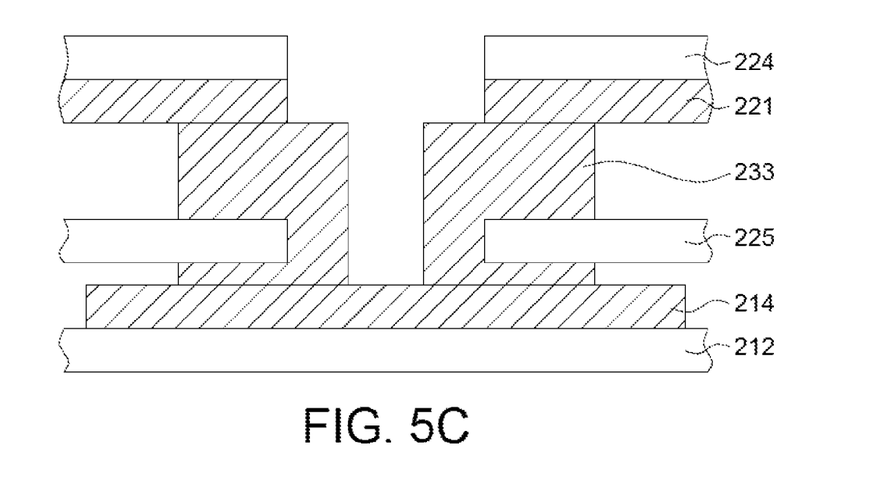
FIG. 5C is a cross-sectional view of a conductive structure according to another embodiment.

Referring to FIG. 5C, a cross-sectional view of a conductive structure 233 according to another embodiment is shown. The conductive structure 233 can be realized by a conductive material such as a tin paste and a conductive adhesive or a conductive piece, and can be used as a medium for electrical transfer between the electrode pattern 214 and the top electrode layer 221 or between the electrode pattern 217 and the bottom electrode layer 222. The conductive structure 233 can be used as the first conductive structure 131, the second conductive structure 132, the third conductive structure 133 or the fourth conductive structure 134 disclosed above.

In an unillustrated embodiment, when the conductive structure 233 is realized by a conductive piece, the effect of electrical connection can be achieved if the conductive piece is extended to the electrode pattern at the edge of the substrate 212 through the leads, and the leads and corresponding electrode pattern are retained or fixed by the conductive piece.

Figure 6A:
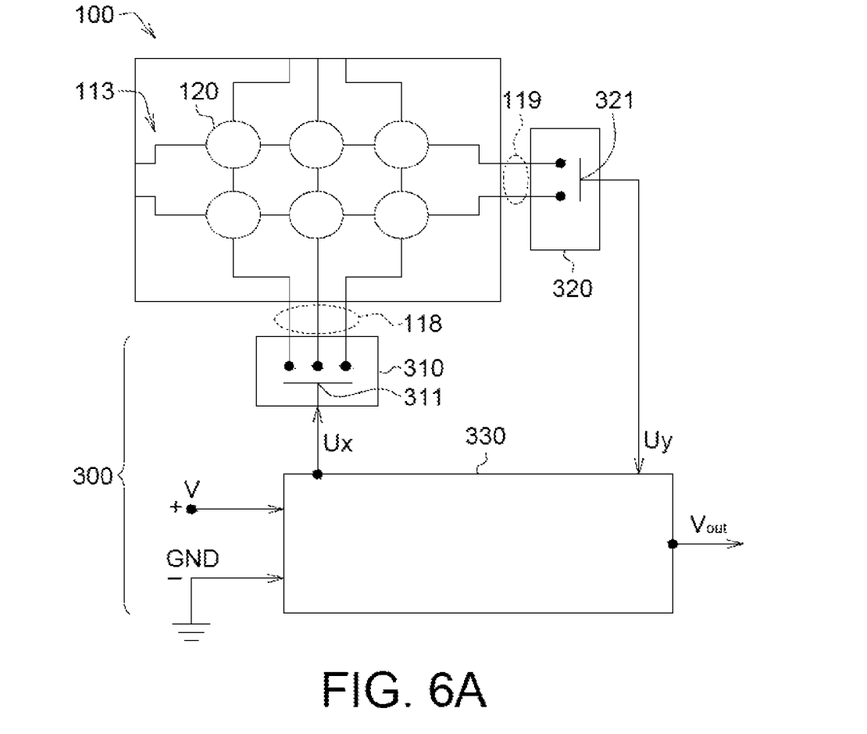
FIGS. 6A and 6B are a schematic diagram and an equivalent circuit diagram of a control module according to an embodiment.
Figure 6B:
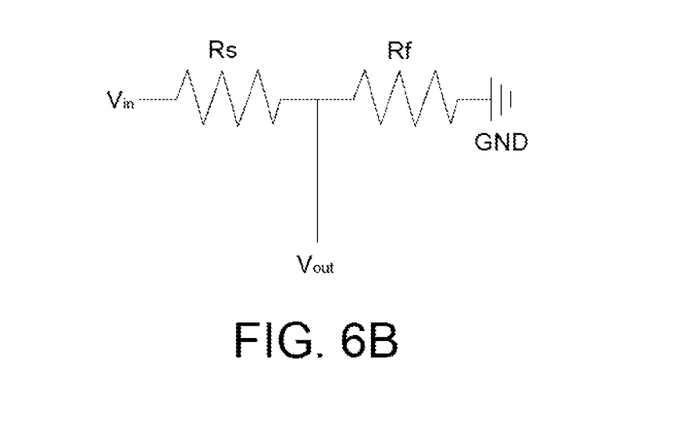

Referring to FIGS. 6A and 6B, a schematic diagram and an equivalent circuit diagram of a control module 300 according to an embodiment are respectively shown. The control module 300 can be used in a monitoring system which detects a surface of an object by using the pressure array sensor module 100. For example, the control module 300 monitors whether the surface of the object is collided or contacted. The control module 300 electrically connects the pressure array sensor module 100. Detailed descriptions of the structure of the pressure array sensor module 100 can be obtained with reference to FIGS. 1A and 1B, and the similarities are not repeated here.

Refer to FIG. 6A. In the present embodiment, the control module 300 includes a first switch circuit 310, a second switch circuit 320 and a voltage detecting unit 330. The first switch circuit 310 has a parallel switch 311 capable of electrically connecting several first signal circuits 118 (exemplified by three signal lines) extended to the first switch circuit 310 from the array electrode 113 at the same time, such that the first signal circuit 118 are mutually connected in parallel, and the top electrode layer of each pressure sensing element 120 electrically connecting the first signal circuit 118 can be mutually conducted. The second switch circuit 320 has a parallel switch 321 capable of concurrently electrically connecting several second signal circuits 119 (exemplified by two signal lines) extended to the second switch circuit 320 from the array electrode 113, such that the second signal circuit 119 are mutually connected in parallel, and the bottom electrode layer of each pressure sensing element 120 electrically connecting the second signal circuit 119 can be mutually conducted. Therefore, when the parallel switch 311 of the first switch circuit 310 conducts the first signal circuits 118 and the parallel switch 321 of the second switch circuit 320 conducts the second signal circuit 119, the pressure sensing elements 120 can be connected in parallel between the first signal circuits 118 and the second signal circuits 119 to generate an equivalent resistance.

In FIG. 6A, the voltage detecting unit 330 includes an input end Ux, an output end Uy and a power source V. The power source V connects the input end Ux to generate an input voltage $V_{in}$. The input end Ux electrically connects the first signal circuits 118 through the first switch circuit 310.

The output end Uy electrically connects the second signal circuits 119 through the second switch circuit 320.

In FIG. 6B, $R_S$ denotes an equivalent resistance of the parallel-connected pressure sensing elements 120, Rf denotes a reference resistance of the voltage detecting unit 330, $V_{in}$ denotes an input voltage of the voltage detecting unit 330, $V_{out}$ denotes an output voltage of the voltage detecting unit 330. In the present embodiment, the output voltage $V_{out}$ of the voltage detecting unit 330 is related to the equivalent resistance Rs of the parallel-connected pressure sensing element 120. When the equivalent resistance increases, the output voltage decreases relatively; when the equivalent resistance decreases, the output voltage increases relatively. Therefore, the output voltage is measured and the equivalent resistance $R_S$ of the parallel-connected pressure sensing element 120 is calculated according to the voltage-division principle. It is determined that the surface of the object is collided or contacted if the equivalent resistance is over a predetermined reference value or has significant change.

Figure 7A:
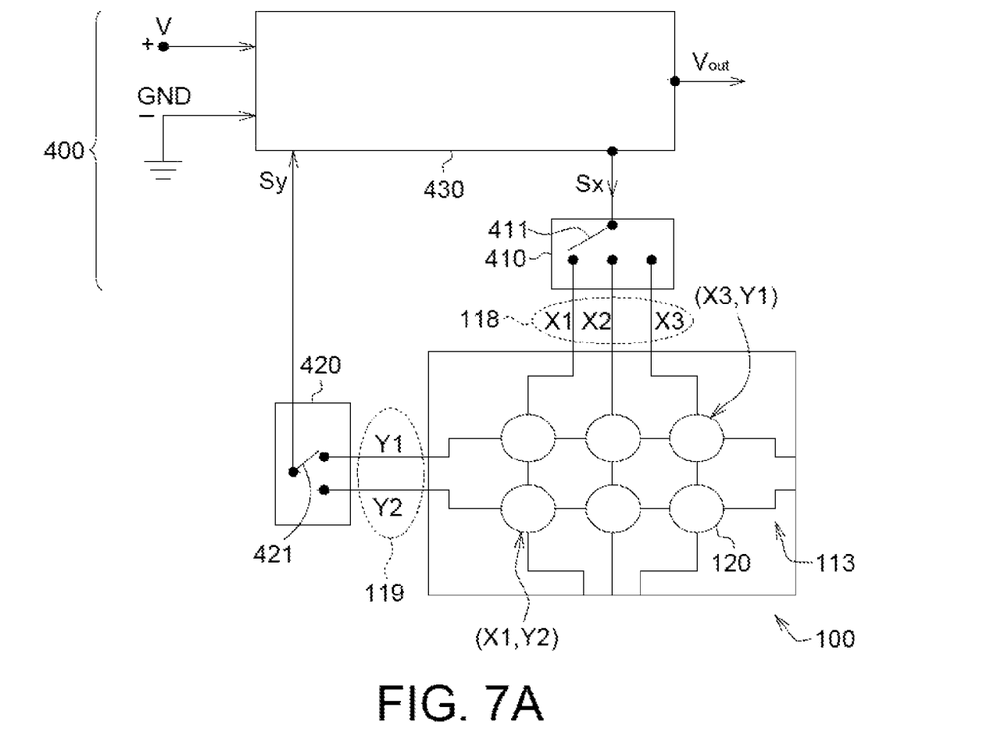
FIGS. 7A and 7B are a schematic diagram and an equivalent circuit diagram of a control module according to an embodiment.
Figure 7B:
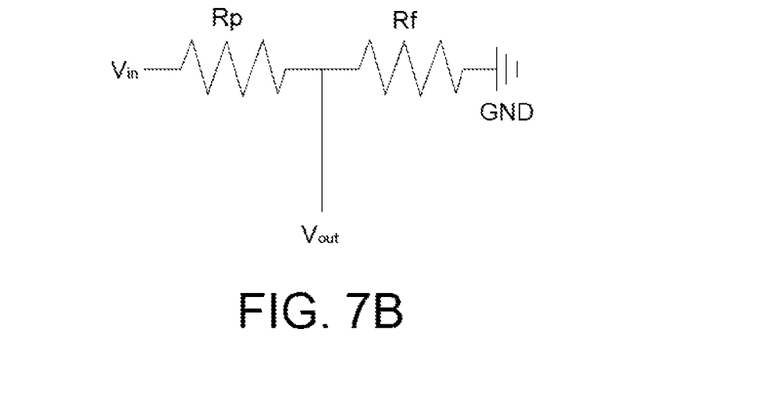

Referring to FIGS. 7A and 7B, a schematic diagram and an equivalent circuit diagram of a control module 400 according to an embodiment are respectively shown. The control module 400 can be used in a monitoring system which performs self-detection or self-diagnosis on the pressure array sensor module 100. The control module 400 electrically connects the pressure array sensor module 100. Detailed descriptions of the structure of the pressure array sensor module 100 can be obtained with reference to FIGS. 1A and 1B, and the similarities are not elaborated here. In the present embodiment, the control module 400 includes a first switch circuit 410, a second switch circuit 420 and a voltage detecting unit 430. The voltage detecting unit 430 includes an input end Sx, an output end Sy and a power source V. The power source V connects the input end Sx to generate an input voltage $V_{in}$.

The scan switch 411 of the first switch circuit 410 selectively and electrically connects one of several first signal circuits 118 extended to the first switch circuit 410 from the array electrode 113, that is, electrically connects the top electrode layer of a pressure sensing element 120 correspondingly connected to the first signal circuit 118. The scan switch 421 of the second switch circuit 420 selectively and electrically connecting one of several second signal circuits 119 extended to the second switch circuit 420 from the array electrode 113, that is, electrically connects the bottom electrode layer of a pressure sensing element 120 correspondingly connected to the second signal circuit 119. Therefore, when the scan switch 411 of the first switch circuit 410 conducts a selected one of the first signal circuits 118 and the scan switch 421 of the second switch circuit 420 conducts a selected one of the second signal circuits 119, a corresponding pressure sensing element 120 disposed at a junction between the selected first signal circuit 118 and the selected second signal circuit 119 will be conducted to generate a resistance. As indicated in FIG. 7A, X1, X2, X3 denote three signal lines used as the first signal circuits 118, and Y1, Y2 denote two signal lines used as the second signal circuits 119. When the signal lines X1 and Y2 are selected, the pressure sensing element 120 disposed at the junction (X1, Y2) is conducted. When the signal lines X3 and Y1 are selected, the pressure sensing element 120 disposed at the junction (X3, Y1) is conducted.

In FIG. 7B, Rp denotes a resistance of a conducted pressure sensing element 120, Rf denotes a reference resistance of the voltage detecting unit 430, $V_{in}$ denotes an input voltage of the voltage detecting unit 430, $V_{out}$ denotes an output voltage of the voltage detecting unit 430. In the present embodiment, the output voltage $V_{out}$ of the voltage detecting unit 430 is related to the resistance $R_p$ of the conducted pressure sensing element 120. When the resistance increases, the output voltage relatively decreases; when the resistance decreases, the output voltage relatively increases. Therefore, by switching the switch addresses of the first and the second switch circuits 410 and 420, the pressure sensing elements 120 are checked in sequence, the output voltage is measured, and the resistance of each conducted pressure sensing element 120 is calculated according to the voltage-division principle. It is determined that the resistor of the pressure sensing element 120 fails if the measured resistance is over a predetermined reference value or has significant change.

Figure 8:
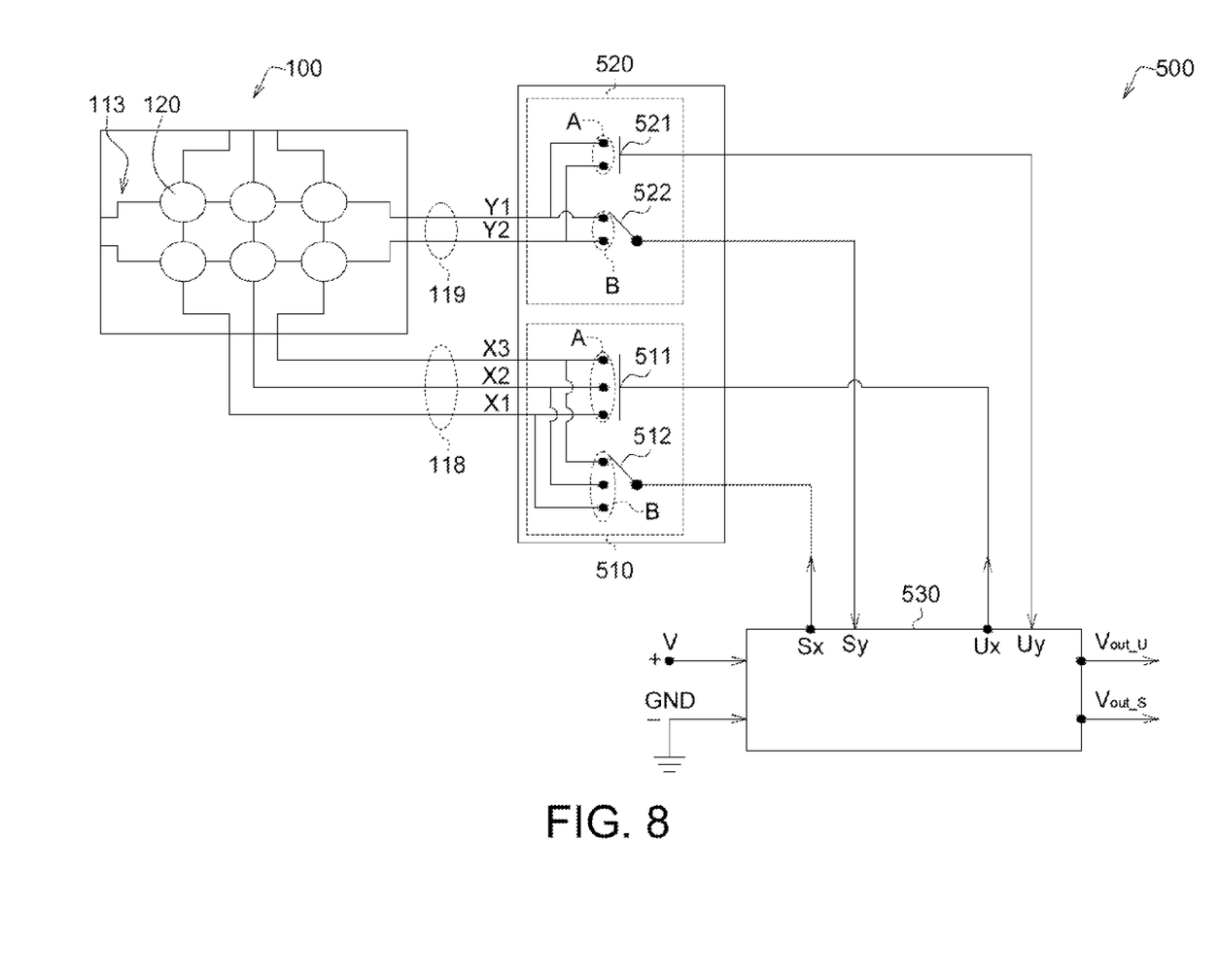
FIG. 8 is a schematic diagram of a control module according to an embodiment.

Referring to FIG. 8, a schematic diagram of a control module 500 according to an embodiment is shown. The control module 500 can be selectively used in a monitoring system which detects a surface of an object by using the pressure array sensor module 100. For example, the control module 500 monitors whether the surface of the object is collided or contacted. The control module 500 can also be selectively used in a monitoring system which performs self-detection or self-diagnosis on the pressure array sensor module 100. In the present embodiment, the control module 500 integrates the switch circuit and the scan circuit (the two circuits required by the two independent monitoring systems disclosed above) into one piece. Since the control module 500 only needs to connect to one set of signal circuit, there is no need to design two independent sets of signal circuits, and the design of circuit layout is greatly simplified.

The control module 500 includes a first switch circuit 510, a second switch circuit 520 and a voltage detecting unit 530. That is, the control module 300 of FIG. 6A and the control module 400 of FIG. 7A are integrated as the control module 500 of FIG. 8. The first switch circuit 510 includes a first parallel switch 511 and a first scan switch 512. The second switch circuit 520 includes a second parallel switch 521 and a second scan switch 522. The first parallel switch 511 can connect several first branch endpoints A of the first signal circuits 118 at the same time, such that the first signal circuits 118 are mutually connected in parallel, and the first scan switch 512 can respectively be conducted at several second branch endpoints B of the first signal circuits 118. However, the first parallel switch 511 and the first scan switch 512 will not be used at the same time. Therefore, each signal line of the first signal circuit 118 has a first branch endpoint A and a second branch endpoint B, such that the first parallel switch 511 and the first scan switch 512 can share the same first signal circuit 118.

Additionally, the second parallel switch 521 can connect several first branch endpoints A of the second signal circuits 119 at the same time, such that the second signal circuit 119 are mutually connected in parallel, and the second scan switch 522 can respectively be conducted at several second branch endpoints B of the second signal circuits 119. However, the second parallel switch 521 and the second scan switch 522 will not be used at the same time. Therefore, each signal line of the second signal circuit 119 has a first branch endpoint A and a second branch endpoint B, such that the second parallel switch 521 and the second scan switch 522 share the same second signal circuit 119.

In an embodiment, when the control module 500 uses the first parallel switch 511 and the second parallel switch 521, the first scan switch 512 and the second scan switch 522 are disabled by the control module 500 and will not work. Conversely, when the control module 500 uses the first scan switch 512 and the second scan switch 522, the first parallel switch 511 and the second parallel switch 521 are disabled by the control module 500 and will not work. Therefore, the first parallel switch 511 and the first scan switch 512 will not be used at the same time, and the second parallel switch 521 and the second scan switch 522 will not be used at the same time.

Details of the operation related to the first parallel switch 511 and the second parallel switch 521 can be obtained with reference to FIGS. 6A and 6B. Since the equivalent resistance of each conducted pressure sensing element 120 can be instantly detected by a collision detection loop of the monitoring system, it is determined that the surface of the object is collided or contacted if the equivalent resistance is over a predetermined reference value or has significant change. In FIG. 8, $V_{out\_U}$ denotes an output voltage of the voltage detecting unit 530 during collision detection.

Details of the operation related to the first scan switch 512 and the second scan switch 522 can be obtained with reference to FIGS. 7A and 7B. Since the resistance of each pressure sensing element 120 conducted by address scanning can be instantly detected by a self-detection loop of the monitoring system, it is determined that the resistor of the pressure sensing element 120 fails if the measured resistance is over a predetermined reference value or has significant change. In FIG. 8, $V_{out\_S}$ denotes an output voltage of the voltage detecting unit 530 during self-detection.

Figure 9:
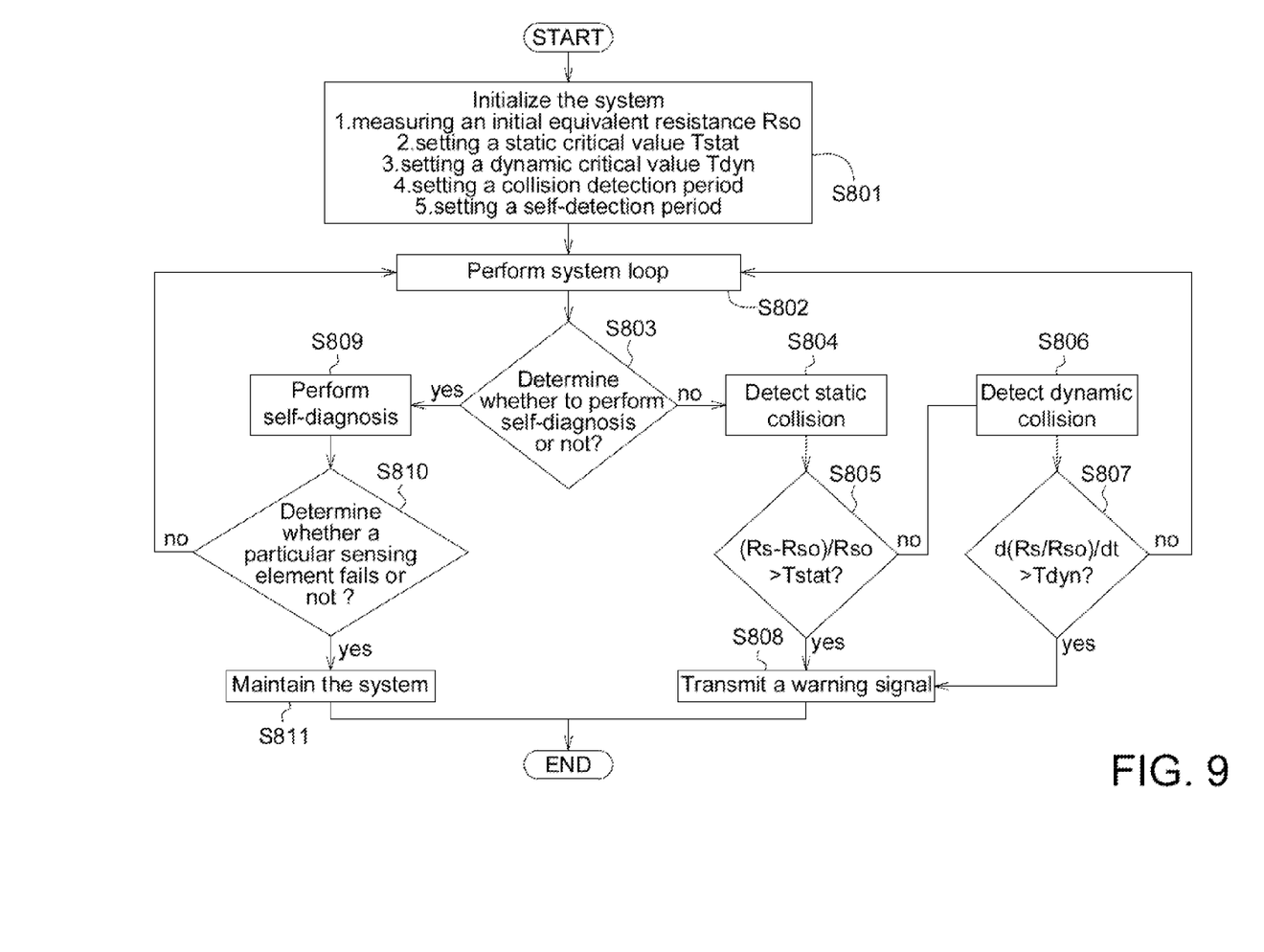
FIG. 9 is a detection flowchart of a collision detection loop and a self-detection loop according to an embodiment.

A detection flowchart of a collision detection loop and a self-detection loop according to an embodiment is disclosed below. Descriptions of related elements are disclosed above, and are not repeated here. Refer to FIG. 9. When the control module 500 detects a surface of an object by using the pressure array sensor module 100, an initialization procedure as illustrated in step S801 is firstly performed. The initialization procedure includes: measuring an initial equivalent resistance Rso of the parallel-connected pressure sensing elements 120, setting a static critical value Tstat, setting a dynamic critical value Tdyn, setting a collision detection period, and setting a self-detection period. In steps S802~S803, system loop starts, and the control module 500 decides whether to perform the collision detection loop or the self-detection loop. The collision detection loop includes a static detection process and/or a dynamic detection process. In the collision detection loop illustrated in steps S804~S808, if a difference or ratio of the equivalent resistance Rs to a predetermined initial equivalent resistance Rso is over a critical value, it is determined that the surface of the object is collided or contacted and a warning signal is transmitted. In the self-detection loop illustrated in steps S809~S811, if the resistance measured by addressing scanning is over a predetermined reference resistance or has significant change, it is determined that the resistor of the pressure sensing elements 120 fails and should be replaced or repaired such that normal operation of the system can be maintained.

In the static detection illustrated in steps S804~S805, the calculation is based on the difference between the measurement of the equivalent resistance Rs of the parallel-connected pressure sensing elements 120 and the initial equivalent resistance Rso. In an embodiment, when a ratio (Rs−Rso)/Rso, that is, a ratio of the difference between the measurement of the equivalent resistance Rs and the initial equivalent resistance Rso to the initial equivalent resistance Rso, is greater than a static critical value Tstat or is within a predetermined range, this implies that collision or contact occurs to the surface of the object. Then, the monitoring system accordingly transmits a warning signal. Conversely, when the ratio (Rs−Rso)/Rso is smaller than the predetermined static critical value Tstat or is within a predetermined range, this implies that either no collision occurs or no contact is beyond an allowable range. Then, the monitoring system does not transmit any warning signals or the process proceeds to step S806 to perform dynamic detection. As long as the condition of the predetermined critical value is satisfied in either one of the static detection and the dynamic detection, a warning signal is transmitted.

In an exemplary example, the static critical value Tstat may range between 10%~50%, 15%~35%, or 20%~40%. The user can set or adjust the static critical value Tstat according to the needs of the monitoring system. Besides, the static detection only performs quantitative detection for static contact or the force applied on the pressure array sensor module 100. To obtain instant variation of the force applied on the pressure array sensor module 100, the dynamic detection as illustrated in steps S806~S807 must be performed.

In the dynamic detection illustrated in steps S806~S807, the differential of the ratio of the equivalent resistance Rs of the parallel-connected pressure sensing elements 120 to the initial equivalent resistance Rso with respect to time is calculated. In an embodiment, when the ratio Rs/Rso is differentiated with respect to time, that is, d (Rs/Rso)/dt, is greater than a dynamic critical value Tdyn or is within a predetermined range, this implies that the surface of the object is collided or contacted. Then, the monitoring system transmits a warning signal. Conversely, when d (Rs/Rso)/dt, is smaller than the dynamic critical value Tdyn or is within a predetermined range, the monitoring system does not need to transmit any warning signals.

In an exemplary example, the dynamic critical value Tdyn may range between 10%/sec~100%/sec, 20%/sec~90%/sec, or 30%/sec~80%/sec. The sampling time is between 0.1~1 sec or 0.3~0.5 sec. The user can set or adjust the dynamic critical value Tdyn according to the needs of the monitoring system.

In step S811, when it is determined that the resistor of a particular pressure sensing element 120 fails, the system can be maintained. For example, the failed pressure sensing element 120 is replaced or the circuit is repaired. Since the pressure sensing elements 120 of the present embodiment are manufactured independently, the manufacturer only needs to replace the failed pressure sensing element 120 without having to manufacture a new circuit board, hence reducing the manufacturing cost.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A pressure array sensor module, comprising:
   an array electrode board, comprising:
     a substrate; and
     an array electrode disposed on the substrate and having a first electrode pattern and a second electrode pattern;
   a plurality of pressure sensing elements respectively disposed on a sensing position of the array electrode board and each pressure sensing element is a separable independent element, wherein each pressure sensing element comprises:
     a top electrode layer having a first lead;
     a bottom electrode layer having a second lead; and at least one pressure sensing layer disposed between the top electrode layer and the bottom electrode layer;
a plurality of first conductive structures electrically connected and vertically conducted to an overlapped portion between each first lead and a corresponding first electrode pattern respectively; and
a plurality of second conductive structures electrically connected and vertically conducted to an overlapped portion between each second lead and a corresponding second electrode pattern respectively.

2. The pressure array sensor module according to claim 1, wherein the first electrode pattern is extended between adjacent two of the pressure sensing elements, and the two adjacent pressure sensing elements are electrically connected through the first electrode pattern and two corresponding first conductive structures.

3. The pressure array sensor module according to claim 1, wherein the second electrode pattern is extended between adjacent two of the pressure sensing elements, and the two adjacent pressure sensing elements are electrically connected through the second electrode pattern and two corresponding second conductive structures.

4. The pressure array sensor module according to claim 1, further comprising:
a plurality of third conductive structures, and
a plurality of fourth conductive structures; wherein
the array electrode further comprises a third electrode pattern and a fourth electrode pattern are disposed on the substrate, wherein each top electrode layer further has a third lead, and each bottom electrode layer further has a fourth lead,
the third conductive structures are electrically connected between each third lead and a corresponding third electrode pattern respectively, and
the fourth conductive structures are electrically connected between each fourth lead and a corresponding fourth electrode pattern respectively.

5. The pressure array sensor module according to claim 4, wherein the third electrode pattern is extended between adjacent two of the pressure sensing elements, and the two adjacent pressure sensing elements are electrically connected through the third electrode pattern and two corresponding third conductive structures.

6. The pressure array sensor module according to claim 4, wherein the fourth electrode pattern is extended between adjacent two of the pressure sensing elements, and the two adjacent pressure sensing elements are electrically connected through the fourth electrode pattern and two corresponding fourth conductive structures.

7. The pressure array sensor module according to claim 4, wherein the top electrode layers of the pressure sensing elements are respectively connected in series between the first electrode pattern and the third electrode pattern through the first conductive structures and the third conductive structures.

8. The pressure array sensor module according to claim 4, wherein the bottom electrode layers of the pressure sensing elements are respectively connected in series between the second electrode pattern and the fourth electrode pattern through the second conductive structures and the fourth conductive structures.

9. The pressure array sensor module according to claim 1, wherein each pressure sensing element further comprises a top substrate, a bottom substrate and a plurality of engaging portions engaging the top substrate and the bottom substrate, and the top electrode layer, the pressure sensing layer and the bottom electrode layer are stacked between the top substrate and the bottom substrate.

10. The pressure array sensor module according to claim 1, wherein the first and the second conductive structures are vertical conductive elements and pass through the pressure sensing elements and the array electrode board.

11. The pressure array sensor module according to claim 1, wherein the array electrode is disposed on one side or two opposite sides of the substrate.

12. A manufacturing method of pressure array sensor module, comprising:
forming an array electrode on one side or two opposite sides of a substrate, wherein the array electrode has a first electrode pattern and a second electrode pattern;
disposing a plurality of pressure sensing elements on the substrate, wherein each pressure sensing element is a separable independent element and each pressure sensing element has a top electrode layer, a bottom electrode layer and at least one pressure sensing layer disposed between the top electrode and the bottom electrode;
electrically connecting and vertically conducting to an overlapped portion between the first lead of each top electrode layer and a corresponding first electrode pattern by a plurality of first conductive structures respectively; and
electrically connecting and vertically conducting to an overlapped portion between the second lead of each bottom electrode layer and a corresponding second electrode pattern by a plurality of second conductive structures respectively.

13. The manufacturing method according to claim 12, wherein the first electrode pattern is extended between adjacent two of the pressure sensing elements, and the two adjacent pressure sensing elements are electrically connected through the first electrode pattern and two corresponding first conductive structures.

14. The manufacturing method according to claim 12, wherein the second electrode pattern is extended between adjacent two of the pressure sensing elements, and the two adjacent pressure sensing elements are electrically connected through the second electrode pattern and two corresponding second conductive structures.

15. The manufacturing method according to claim 12, wherein the array electrode further comprises a third electrode pattern and a fourth electrode pattern disposed on the substrate, each top electrode layer further has a third lead, each bottom electrode layer further has a fourth lead, and the manufacturing method of pressure array sensor module further comprises:
electrically connecting each third lead and a corresponding third electrode pattern by a plurality of third conductive structures respectively; and
electrically connecting each fourth lead and a corresponding fourth electrode pattern by a plurality of fourth conductive structures respectively.

16. The manufacturing method according to claim 15, wherein the third electrode pattern is extended between adjacent two of the pressure sensing elements, and the two adjacent pressure sensing elements are electrically connected through the third electrode pattern and two corresponding third conductive structures.

17. The manufacturing method according to claim 15, wherein the fourth electrode pattern is extended between adjacent two of the pressure sensing elements, and the two adjacent pressure sensing elements are electrically connected through the fourth electrode pattern and two corresponding fourth conductive structures.

18. The manufacturing method according to claim 15, wherein the top electrode layers of the pressure sensing elements are respectively connected in series between the first electrode pattern and the third electrode pattern through the first conductive structures and the third conductive structures.

19. The manufacturing method according to claim 15, wherein the bottom electrode layers of the pressure sensing elements are respectively connected in series between the second electrode pattern and the fourth electrode pattern through the second conductive structures and the fourth conductive structures.

20. The manufacturing method according to claim 12, wherein the first and the second conductive structures are vertical conductive elements.

21. A monitoring system, comprising:
the pressure array sensor module according to claim 1; and
a control module, comprising:
a first switch circuit, comprising a first parallel switch capable of electrically connecting a plurality of first signal circuits extended to the first switch circuit from the array electrode at the same time, such that the first signal circuits are mutually connected in parallel;
a second switch circuit, comprising a second parallel switch capable of concurrently electrically connecting a plurality of second signal circuits extended to the second switch circuit from the array electrode at the same time, such that the second signal circuits are mutually connected in parallel; and
a voltage detecting unit having an input end and an output end, wherein the input end electrically connects the first signal circuits through the first switch circuit, the output end electrically connects the second signal circuits through the second switch circuit, the input end has an input voltage, the output end has an output voltage, and the voltage detecting unit detects an equivalent resistance of the pressure sensing elements connected in parallel between the first signal circuits and the second signal circuits according to the input voltage and the output voltage.

22. The monitoring system according to claim 21, wherein
the first switch circuit further comprises a first scan switch which selectively and electrically connects one of the first signal circuits;
a second switch circuit further comprises a second scan switch which selectively and electrically connects one of the second signal circuits;
the input end electrically connects a selected one of the first signal circuits through the first scan switch, the output end electrically connects a selected one of the second signal circuits through the second scan switch, the input end has an input voltage, the output end has an output voltage, and the voltage detecting unit detects a resistance of a corresponding pressure sensing element at a junction between the selected first signal circuit and the selected second signal circuit according to the input voltage and the output voltage.

23. The monitoring system according to claim 22 used for performing a collision detection loop or a self-detection loop on the pressure array sensor module, wherein the collision detection loop detects a variation in the equivalent resistance of the pressure sensing elements with respect to an initial equivalent resistance, and the self-detection loop detects a variation in the resistance of a corresponding pressure sensing element with respect to a reference resistance,
wherein, the first parallel switch and the first scan switch share but do not use the first signal circuits at the same time;
the second parallel switch and the second scan switch share but do not use the second signal circuits at the same time.

24. A monitoring method, comprising:
providing a control module and a pressure array sensing module, wherein the pressure array sensor module is disposed on a surface of an object; and
determining whether to perform a collision detection loop or a self-detection loop on the pressure array sensor module by using the control module;
when the control module selects to perform the collision detection loop by using the monitoring system according to claim 23, the collision detection loop detects a variation in the equivalent resistance of the pressure sensing elements with respect to an initial equivalent resistance;
when the control module selects to perform the self-detection loop by using the monitoring system according to claim 23, the self-detection loop detects the variation in each resistance of the scanned pressure sensing elements with respect to a reference resistance,
wherein, the first parallel switch and the first scan switch share but do not use the first signal circuits at the same time;
the second parallel switch and the second scan switch share but do not use the second signal circuits at the same time.

25. The monitoring method according to claim 24, wherein the collision detection loop comprises a static detection process, which calculates a difference between the equivalent resistance of the pressure array sensing elements connected in parallel and the initial equivalent resistance, and when a ratio of the difference to the initial equivalent resistance is greater than a critical value, this implies that a collision or a contact is generated on the surface of the object.

26. The monitoring method according to claim 24, wherein the collision detection loop comprises a dynamic detection process, which calculates differential of a ratio of the equivalent resistance of the pressure array sensing elements connected in parallel to the initial equivalent resistance with respect to time, and when the differential of the ratio with respect to time is greater than a critical value, this implies that a collision or contact is generated on the surface of the object.

* * * * *